United States Patent
Deshmukh et al.

(10) Patent No.: US 9,421,165 B2
(45) Date of Patent: Aug. 23, 2016

(54) ORAL CONTROLLED RELEASE PHARMACEUTICAL COMPOSITIONS OF BEPOTASTINE

(75) Inventors: Ashish Ashokrao Deshmukh, Maharashtra (IN); Pravin Meghrajji Bhutada, Maharashtra (IN); Sajeev Chandran, Maharashtra (IN); Shirishkumar Kulkarni, Maharashtra (IN)

(73) Assignee: LUPIN LIMITED, Mumbai, Maharashtra (IN)

( * ) Notice: Subject to any disclaimer, the term of this patent is extended or adjusted under 35 U.S.C. 154(b) by 387 days.

(21) Appl. No.: 13/982,561

(22) PCT Filed: Feb. 3, 2012

(86) PCT No.: PCT/IB2012/050506
§ 371 (c)(1),
(2), (4) Date: Jul. 30, 2013

(87) PCT Pub. No.: WO2012/104818
PCT Pub. Date: Aug. 9, 2012

(65) Prior Publication Data
US 2013/0317063 A1    Nov. 28, 2013

(30) Foreign Application Priority Data
Feb. 3, 2011    (IN) .............................. 157/KOL/2011

(51) Int. Cl.
| | |
|---|---|
| *A61K 9/00* | (2006.01) |
| *A61K 9/20* | (2006.01) |
| *A61K 9/24* | (2006.01) |
| *A61K 9/28* | (2006.01) |
| *A61K 31/4545* | (2006.01) |

(52) U.S. Cl.
CPC ........... *A61K 9/0053* (2013.01); *A61K 9/0004* (2013.01); *A61K 9/209* (2013.01); *A61K 9/2018* (2013.01); *A61K 9/2054* (2013.01); *A61K 9/2072* (2013.01); *A61K 9/2086* (2013.01); *A61K 9/2846* (2013.01); *A61K 9/2866* (2013.01); *A61K 31/4545* (2013.01)

(58) Field of Classification Search
USPC ...................................................... 514/318
See application file for complete search history.

(56) References Cited

U.S. PATENT DOCUMENTS

| | | |
|---|---|---|
| 4,929,618 A | 5/1990 | Koda et al. |
| 6,638,534 B1 | 10/2003 | Ishibashi et al. |
| 6,692,769 B1 | 2/2004 | Ishibashi et al. |

FOREIGN PATENT DOCUMENTS

| | | |
|---|---|---|
| EP | 1 961 413 | 8/2008 |
| JP | 2006-45134 | 2/2006 |
| JP | 2011-46750 | 3/2011 |
| WO | WO 2008/027350 | 3/2008 |

OTHER PUBLICATIONS

International Search Report and Written Opinion from International Application No. PCT/IB2012/050506 mailed Jul. 23, 2012.

*Primary Examiner* — Samantha Shterengarts
(74) *Attorney, Agent, or Firm* — Merchant & Gould P.C.

(57) ABSTRACT

The present invention relates to oral controlled release pharmaceutical compositions comprising Bepotastine. The oral controlled release pharmaceutical composition comprises Bepotastine or pharmaceutically acceptable salts thereof and at least one release controlling agent. The present invention also provides the use of oral controlled release pharmaceutical compositions of Bepotastine for the treatment of allergic rhinitis and for the treatment of pruritus caused by urticaria.

16 Claims, 5 Drawing Sheets

ORAL CONTROLLED RELEASE PHARMACEUTICAL COMPOSITIONS OF BEPOTASTINE

FIELD OF THE INVENTION

The present invention relates to oral controlled release pharmaceutical compositions comprising Bepotastine. The present invention also provides the use of oral controlled release pharmaceutical compositions of Bepotastine for the treatment of allergic rhinitis and for the treatment of pruritus caused by urticaria.

BACKGROUND OF THE INVENTION

Allergic rhinitis is a symptomatic disorder of the nose caused by exposure to allergens, which induce an IgE mediated inflammation of the membranes lining the nose. Typical symptoms of allergic rhinitis include running nose, sneezing, nasal blockage and itchy nose. In addition, allergic rhinitis is often associated with asthma and is a risk factor for developing asthma. Pruritus or itch is defined as an unpleasant sensation of the skin that provokes the urge to scratch. It is a characteristic feature of many skin diseases like urticaria. Urticaria is a kind of skin rash notable for pale red, raised itchy bumps which is frequently caused by allergic reactions.

Antihistamines are common first-line treatment for the symptoms of allergic rhinitis by blocking the action of histamine, a chemical released by the immune system in allergic reactions. Antihistamines that bind to the histamine 1 receptor (H1) serve as important therapeutic agents to counter the effects of histamine in the skin. H1 antihistamines have been proven to be effective at reversing the pruritus and cutaneous lesions of chronic urticaria.

Bepotastine (+)-(S)-4-[4-[(4-Chlorophenyl)(2-pyridyl)methoxyl]piperidinol]butyric acid is an anti-allergic having an antihistamine action. Bepotastine was disclosed in U.S. Pat. No. 4,929,618. Bepotastine is a non-sedative selective antagonist of H1-histamine receptor and exhibits control of eosinophil migration into inflamed tissues. The half life of Bepotastine is 2.4±0.1 hour.

Bepotastine besilate is commercially available as Talion film coated immediate release tablets 5 mg and 10 mg and as Talion orally disintegrating tablets 5 mg and 10 mg in Japan.

The dosing regimen recommended for Bepotastine requires twice daily administration in order to maintain a constant therapeutic level of Bepotastine. Twice daily administration of the immediate release dosage of Bepotastine results in peak-trough profile due to short half life and rapid elimination of the drug. High systemic exposure ($C_{max}$) of the drug may result in systemic side-effects.

Controlled release pharmaceutical compositions offer many advantages over immediate-release pharmaceutical compositions. Apart from increasing the patient compliance by decreasing the frequency of administration, the controlled release pharmaceutical compositions maintain effective blood levels for longer period of time and causes reduction in systemic drug exposure related side effects.

U.S. Pat. No. 6,692,769 discloses sustained release particles comprising a drug containing core coated with a mixed coating of a hydrophobic organic compound-water insoluble polymer and a preparation method of tablets using these sustained release particles.

U.S. Pat. No. 6,638,534 discloses unit dose composition capable of releasing a medicinal substance at a targeted site in the intestine. The composition comprises a core material containing a medicinal substance coated with a mixed film of hydrophobic organic compound and enteric polymer.

Due to short half-life in vivo, Bepotastine and its pharmaceutically acceptable salts as currently formulated are commonly administered twice daily. It has been observed, surprisingly that it is possible to modify the release profile of Bepotastine Besilate, obtaining a controlled release of Bepotastine up to 16 hours.

The controlled release pharmaceutical compositions of Bepotastine are administered less frequently and may alleviate the above disclosed problems associated with conventional immediate release compositions.

The specification discloses oral controlled release pharmaceutical compositions of Bepotastine or pharmaceutically acceptable salts thereof. The oral controlled release pharmaceutical compositions of the invention provide release of Bepotastine in a controlled manner over a prolonged or extended period of time. The oral controlled release pharmaceutical compositions of the invention are substantially bioequivalent to two immediate release tablets of Bepotastine. Such pharmaceutical compositions also offer the advantage of once-a-day dosing of Bepotastine, increased patient compliance, ease of manufacturing, high throughput of manufacturing and easy scale-up, etc.

SUMMARY OF THE INVENTION

In accordance, one embodiment discloses oral controlled release pharmaceutical compositions comprising Bepotastine or pharmaceutically acceptable salts thereof and at least one release controlling agent.

Another embodiment discloses oral controlled release pharmaceutical compositions comprising Bepotastine or pharmaceutically acceptable salts thereof and release controlling agent, selected from hydrophilic release controlling agents, hydrophobic release controlling agents or mixtures thereof.

Yet another embodiment discloses oral controlled release pharmaceutical compositions of Bepotastine or pharmaceutically acceptable salts thereof, wherein the compositions exhibit in vitro release of Bepotastine not less than about 50% in 12 hours, when dissolution is carried out in 6.8 pH Phosphate Buffer, USP apparatus Type II (Paddle) at 50 rpm or USP apparatus Type I (Basket) at 100 rpm.

Yet another embodiment discloses oral controlled release pharmaceutical compositions of Bepotastine or pharmaceutically acceptable salts thereof, wherein the compositions exhibit in vitro release of Bepotastine not less than about 70% in 12 hours when dissolution is carried out in 0.1 N Hydrochloric acid, USP apparatus Type II (Paddle) at 50 rpm or in USP apparatus Type I (Basket) at 100 rpm.

Yet another embodiment discloses oral controlled release pharmaceutical compositions of Bepotastine or pharmaceutically acceptable salts thereof which demonstrate a maximum serum concentration equivalent to two immediate release tablet of Bepotastine and maintains a therapeutically effective blood concentration of Bepotastine for the duration of at least 24 hours.

Yet another embodiment provides oral controlled release pharmaceutical compositions comprising Bepotastine or pharmaceutically acceptable salts thereof and at least one release controlling agent, wherein pharmaceutical composition administered once daily, is substantially bioequivalent to conventional immediate release composition of Bepotastine administered twice daily.

Yet another embodiment provides oral controlled release pharmaceutical compositions comprising Bepotastine or pharmaceutically acceptable salts thereof and at least one release controlling agent, wherein pharmaceutical compositions exhibit relative bioavailability based on the area under the plasma concentration curve (AUC) for the 24 hours after once a day administration in human subjects, of between about 50 to about 150 compared with commercially available Talion immediate release tablets containing Bepotastine administered twice daily.

Yet another provides oral controlled release pharmaceutical compositions comprising Bepotastine or pharmaceutically acceptable salts thereof and at least one release controlling agent, wherein pharmaceutical compositions exhibit a relative Cmax, after once a day administration in human subjects, of between about 50 to about 150 compared with commercially available Talion immediate release tablets containing Bepotastine administered twice daily.

Yet another embodiment provides oral controlled release pharmaceutical compositions comprising Bepotastine or pharmaceutically acceptable salts thereof and at least one release controlling agent wherein pharmaceutical composition is bioequivalent to conventional immediate release composition of Bepotastine administered twice daily under fed conditions where bioequivalence is established by (a) a 90% confidence interval for AUC which is between 80% and 125%, and (b) a 90% confidence interval for $C_{max}$, which is between 80% and 125%.

Yet another embodiment discloses the use of oral controlled release pharmaceutical compositions of Bepotastine or pharmaceutically acceptable salts thereof for the treatment of allergic rhinitis and treatment of pruritus caused by urticaria.

DETAILED DESCRIPTION OF THE INVENTION

Figure 1:
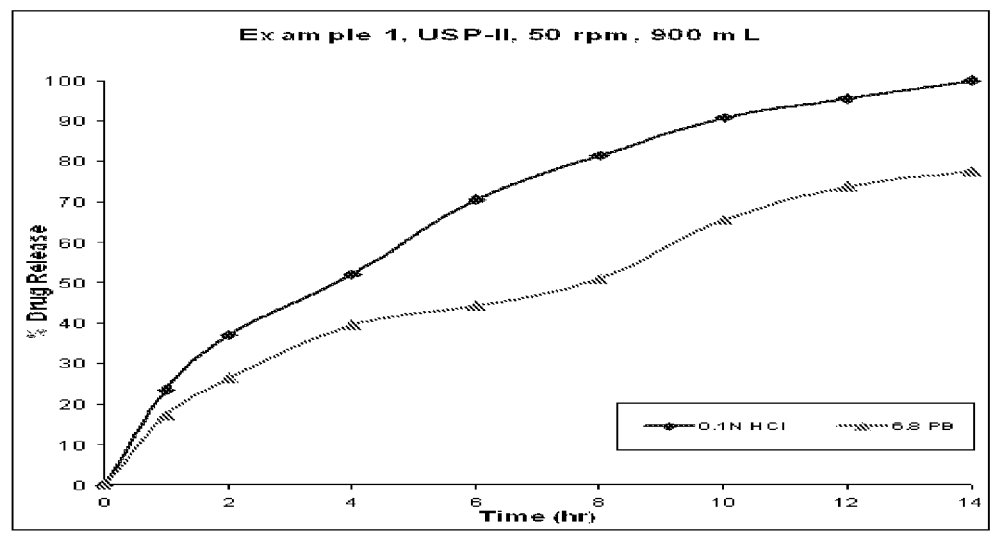
FIG. 1: shows a release profile of controlled release pharmaceutical composition of Bepotastine of example 1, in 900 ml of 0.1N HCl and in 900 mL of pH 6.8 Phosphate Buffer, USP apparatus Type II (Paddle) at 50 rpm for 14 hrs.
Figure 2:
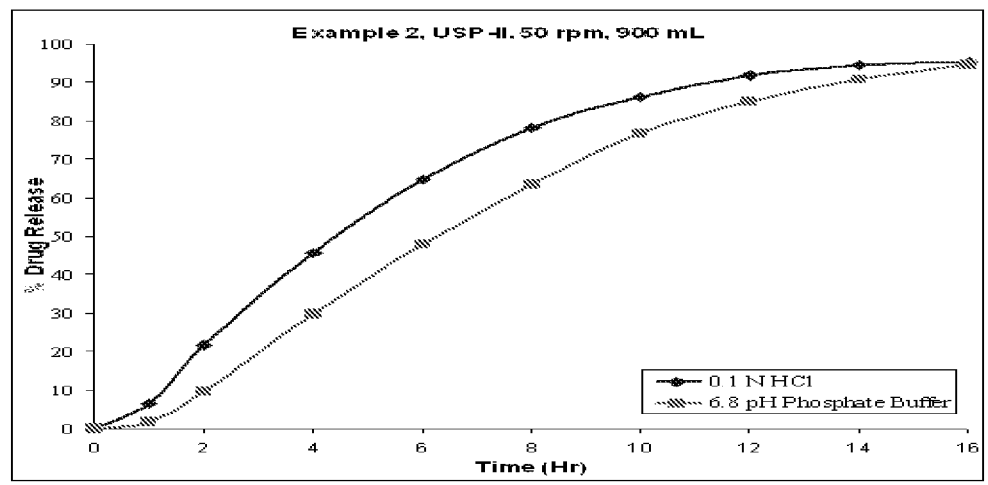
FIG. 2: shows a release profile of controlled release pharmaceutical composition of Bepotastine of example 2, in 900 ml of 0.1N HCl and in 900 mL of pH 6.8 Phosphate Buffer, USP apparatus Type II (Paddle) at 50 rpm for 16 hrs.
Figure 3:
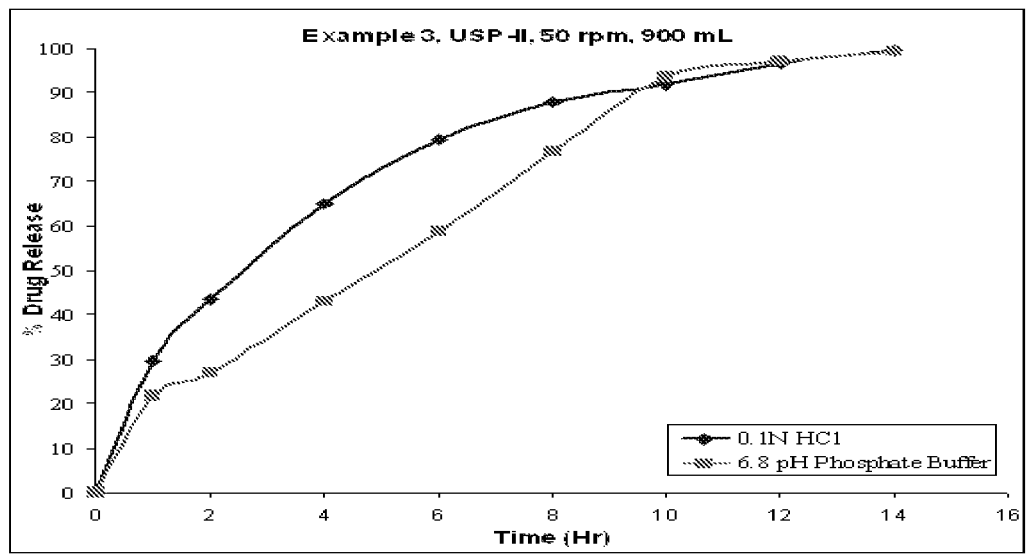
FIG. 3: shows a release profile of controlled release pharmaceutical composition of Bepotastine of example 3, in 900 ml of 0.1N HCl and in 900 mL of pH 6.8 Phosphate Buffer, USP apparatus Type II (Paddle) at 50 rpm for 14 hrs.
Figure 4:
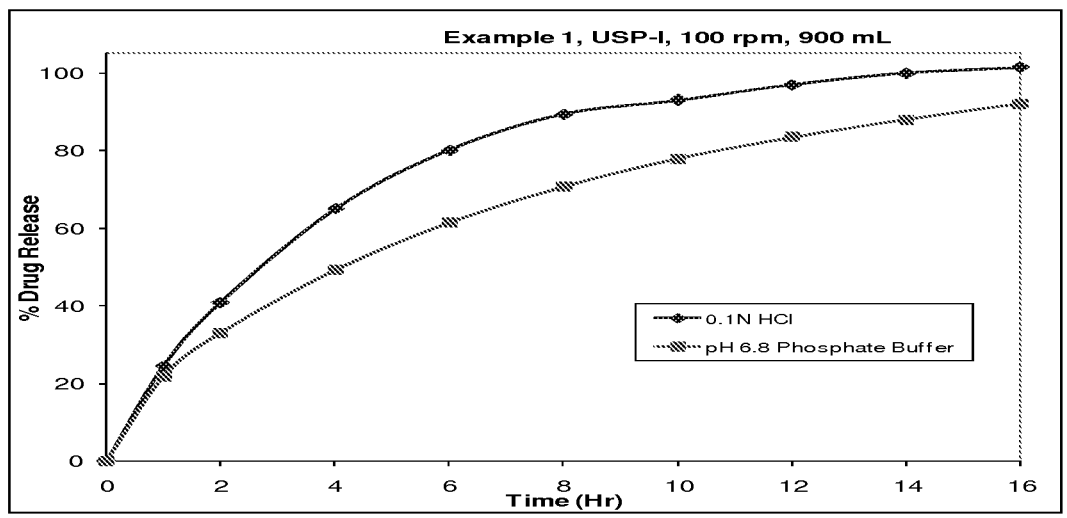
FIG. 4: shows a release profile of controlled release pharmaceutical composition of Bepotastine of example 1, in 900 ml of 0.1N HCl and in 900 mL of pH 6.8 Phosphate Buffer, USP apparatus Type I (Basket) at 100 rpm for 16 hrs.
Figure 5:
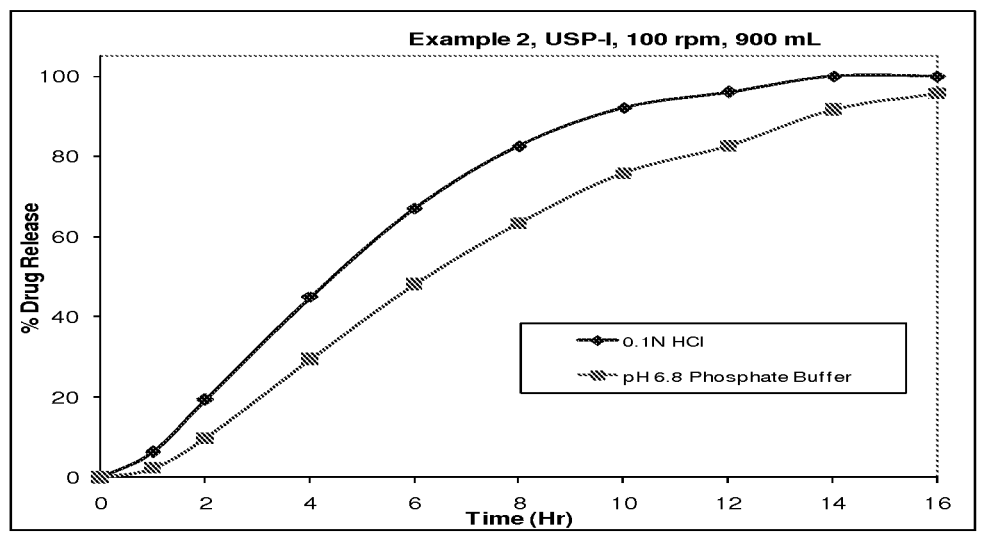
FIG. 5: shows a release profile of controlled release pharmaceutical composition of Bepotastine of example 2, in 900 ml of 0.1N HCl and in 900 mL of pH 6.8 Phosphate Buffer, USP apparatus Type I (Basket) at 100 rpm for 16 hrs.
Figure 6:
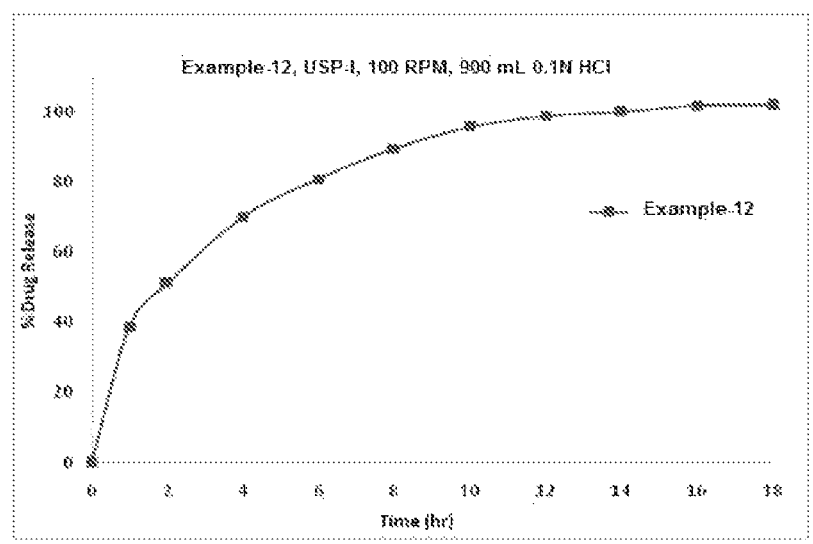
FIG. 6: shows a release profile of controlled release pharmaceutical composition of Bepotastine of example 12, in 900 ml of 0.1N HCl USP apparatus Type I (Basket) at 100 rpm for 18 hrs.
Figure 7:
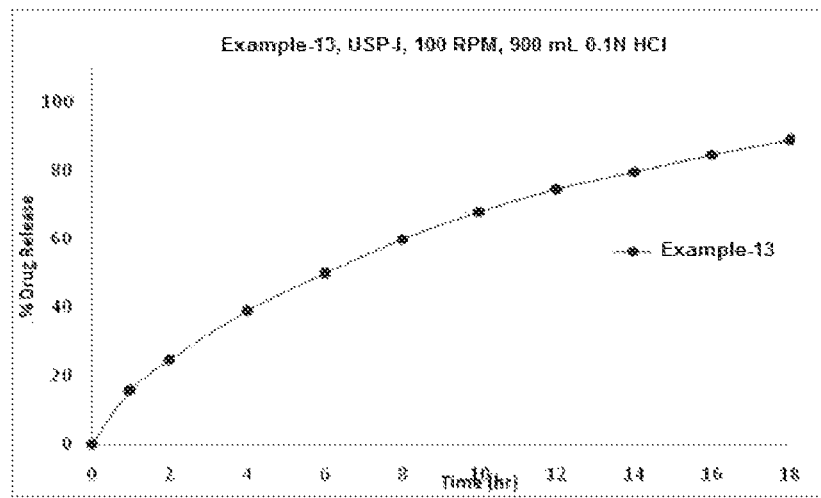
FIG. 7: shows a release profile of controlled release pharmaceutical composition of Bepotastine of example 13, in 900 ml of 0.1N HCl USP apparatus Type I (Basket) at 100 rpm for 18 hrs.
Figure 8:
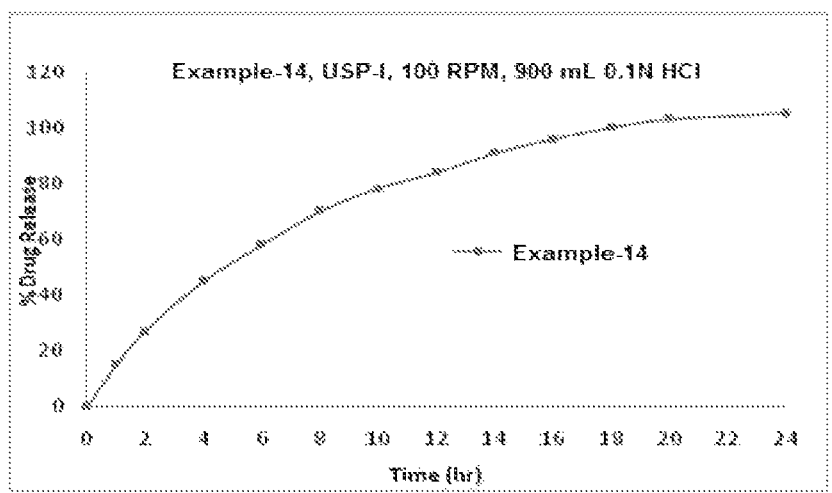
FIG. 8: shows a release profile of controlled release pharmaceutical composition of Bepotastine of example 14, in 900 ml of 0.1N HCl USP apparatus Type I (Basket) at 100 rpm for 24 hrs.
Figure 9:
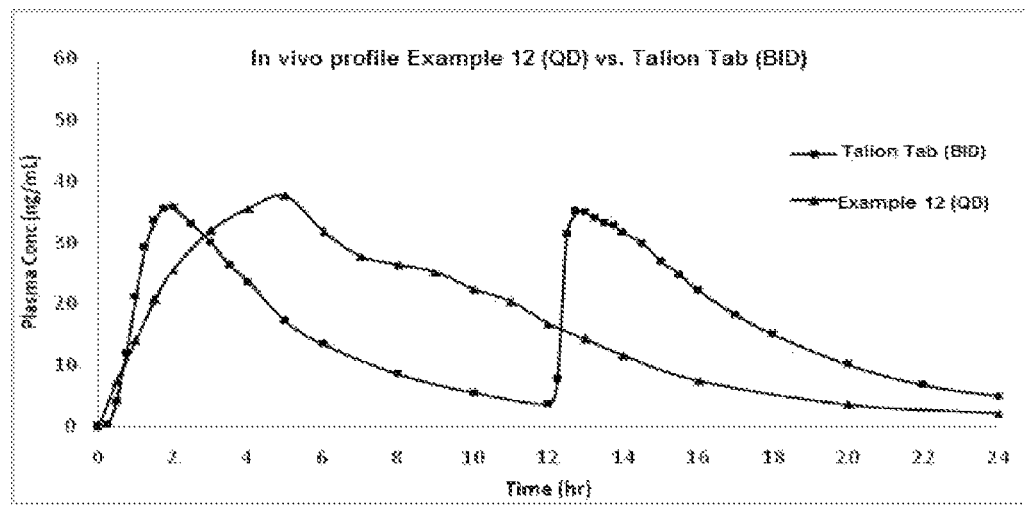
FIG. 9: shows the comparative Bepotastine plasma concentration (ng/ml) over a period of 24 hours for (a) a single dose of tablet prepared according to example 12 and (b) Talion® 5 mg immediate release tablet administered twice daily under fed condition.
Figure 10:
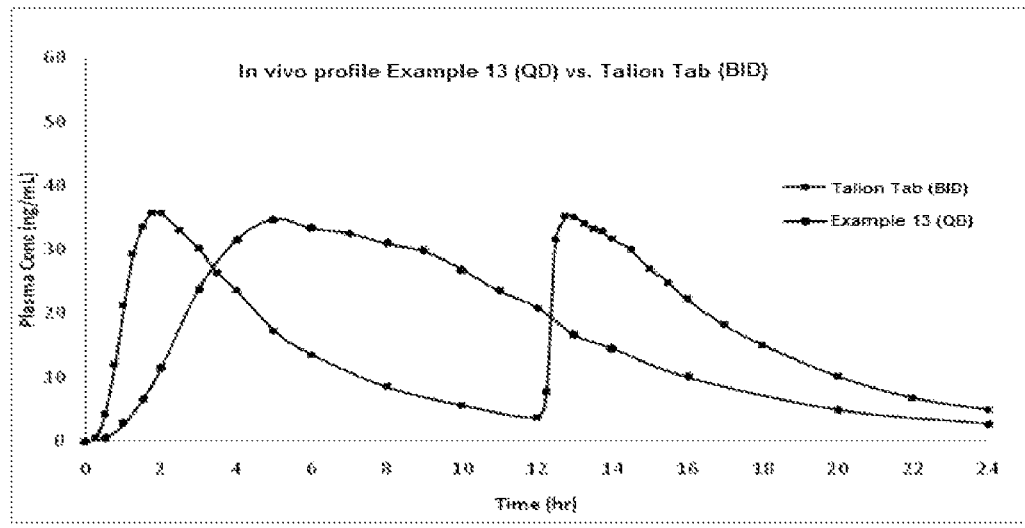
FIG. 10: shows the comparative Bepotastine plasma concentration (ng/ml) over a period of 24 hours for (a) a single dose of tablet prepared according to example 13 and (b) Talion® 5 mg immediate release tablet administered twice daily under fed condition.

The specification discloses oral controlled release pharmaceutical compositions of Bepotastine or pharmaceutically acceptable salts thereof which deliver Bepotastine in a controlled manner over a period or extended period of time.

The specification discloses oral controlled release pharmaceutical compositions comprising Bepotastine or pharmaceutically acceptable salts thereof and release controlling agent.

The amount of Bepotastine or pharmaceutically acceptable salts thereof to be used ranges from about 5 to about 40 mg. In a preferred embodiment the amount of Bepotastine or pharmaceutically acceptable salts thereof to be used ranges from about 5 to about 25 mg. In another embodiment the amount of Bepotastine or pharmaceutically acceptable salts thereof to be used ranges from about 5 to about 20 mg.

As used herein "Bepotastine" encompasses free base, pharmaceutically acceptable salts, pharmacologically active metabolites of Bepotastine and their pharmaceutically acceptable salts, hydrates, its enantiomers or its racemates unless otherwise noted.

The pharmaceutically acceptable salts include but are not limited to salts of inorganic acids (e.g. sulfate, monohydrobromide, etc) and salts of organic acids (e.g. besilate, monobenzoate, monomesilate, fumarate, maleate, mandelate, succinate, tartrate, lactate, malate, fendizoate, etc). Preferably, Bepotastine is used as Bepotastine besilate.

The specification discloses oral controlled release pharmaceutical compositions comprising Bepotastine or pharmaceutically acceptable salts thereof, and release controlling agent and optionally pharmaceutically acceptable excipients.

The term "oral controlled release pharmaceutical compositions" herein refers to any composition which comprises Bepotastine and which is formulated to provide a longer and relatively uniform release of the medication than is ordinarily experienced after administration of a corresponding immediate release composition comprising the same drug in the same amount. "Controlled release" can mean anything which is not 'immediate release' and is exchangeable with for example, 'extended release", "sustained release", "prolonged release", "programmed release", "time release", "rate controlled" or "pulsed-release" at a particular time.

The release controlling agent may be selected from hydrophilic release controlling agent, hydrophobic release controlling agent, or mixtures thereof.

The hydrophilic release controlling agent may be selected from, but not limited to, hydroxypropyl methylcellulose (HPMC), hydroxypropyl cellulose (HPC), polyethylene oxide, polyvinyl alcohol, polyvinylpyrrolidone, xanthan gum, guar gum, chitosan and its derivatives, carbomer, carrageenan, carboxymethyl cellulose, sodium alginate, polyglycolized glycerides, polyethyleneglycol, or mixtures thereof.

The hydrophobic release controlling agent may be selected from, but not limited to, polyvinyl acetate dispersion, ethyl cellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), and poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) and copolymers, waxes such as beeswax, carnauba wax, paraffin wax, microcrystalline wax, and ozokerite; fatty alcohols such as cetostearyl alcohol, stearyl alcohol, cetyl alcohol and myristyl alcohol, and fatty acid esters such as glyceryl monostearate; glycerol monooleate, acetylated monoglycerides, tristearin, tripalmitin, cetyl esters wax, glyceryl palmitostearate, glyceryl behenate, zein and hydrogenated vegetable oils or mixtures thereof.

The amount of release controlling agent may range from about 2% to about 90% by weight of the composition, preferably from about 10% to about 70% by weight of the composition and more preferably from about 15% to about 50% by weight of the composition.

The pharmaceutical compositions of Bepotastine are prepared using one or more release controlling agent being present in the core, and/or in the coating layer. Preferably the release controlling agent is present in the core.

The term "oral controlled release pharmaceutical compositions" is not restricted to any particular type of composition. Various types of controlled release pharmaceutical compositions may be used for embodying the invention. The pharmaceutical compositions of the invention include but are not limited to, solid oral pharmaceutical compositions that encompass one or more individual units. The individual units may be in the form of granules, pellets, minitablets or beads. Granules, pellets, minitablets or beads of the invention can be filled into a capsule, sachet or can be compressed into a tablet.

Controlled release pharmaceutical compositions may be prepared by any conventional techniques and not restricted to, dry granulation, wet granulation, melt granulation, direct compression, extrusion-spheronization or compression coating.

The pharmaceutically acceptable excipients include but are not limited to diluents, binders, solubility enhancing agents, pH modifier, osmagents, gas generating agents, lubricants and glidants known to person skilled in the art.

Diluent may be any pharmaceutically acceptable, non-toxic diluent. Examples of diluents include but are not limited to lactose, microcrystalline cellulose, starch, calcium hydrogen phosphate, mannitol, fructose, dextrose, sucrose and maltose.

Examples of binders include polyvinyl pyrrolidone, low substituted hydroxypropyl methyl cellulose, hydroxypropyl cellulose, starch, sugar, gums and the like.

Examples of solubility enhancing agents include surfactants. The surfactants may be any of the known pharmaceutically acceptable surfactants, including nonionic, anionic and cationic surfactants.

Examples of pH modifiers include pharmaceutically acceptable organic acids. Examples include but are not limited to fumaric acid, succinic acid, malonic acid, oxalic acid, tartaric acid, adipic acid and malic acid.

Examples of osmagents include mannitol, urea, sorbitol, sucrose, sodium chloride, potassium carbonate, calcium chloride, sodium acetate, magnesium sulfate, magnesium chloride, lithium chloride, sodium carbonate, mixtures thereof, and the like.

Gas generating agents may be selected from carbonates such as calcium carbonate, bicarbonates such as sodium or potassium bicarbonate, sulfites such as sodium sulfite, sodium bisulfite, or sodium metabisulfite, and the like. These salts may be used alone or in combination with an acid source as a gas generating couple. The acid source may be an edible organic acid, a salt of an edible organic acid, or mixtures thereof. Examples of organic acids that may be used include citric acid, malic acid, succinic acid, tartaric acid, fumaric acid, maleic acid, ascorbic acid, glutamic acid, and their salts, and mixtures thereof.

Lubricants may be, for example, magnesium stearate, stearic acid, calcium stearate, sodium stearyl fumarate, sodium benzoate or the like.

Glidants may be, for example, colloidal silicon dioxide, talc or the like.

In one embodiment, oral controlled release pharmaceutical composition is in the form of matrix comprising Bepotastine or pharmaceutically acceptable salts thereof, release controlling agents and suitable pharmaceutical excipient which is optionally coated with release controlling agent. Such a coating preferably comprises a hydrophobic release controlling agent and a pore-former.

In another embodiment, oral controlled release pharmaceutical compositions may be formulated in the form of bioadhesive matrix system wherein Bepotastine is dissolved and/or dispersed in a matrix system with selective, high efficacy delivery to specific regions of the gastrointestinal tract, which includes Bepotastine and release controlling agents. The release controlling agent may also work as bioadhesive agents.

As used herein "bioadhesive" refers to the ability of pharmaceutical composition to adhere to a mucosal biological surface for an extended period of time.

In another embodiment, oral controlled release pharmaceutical composition comprises a core comprising Bepotastine, release controlling agent and a gas generating agent, said core being capable of swelling and achieving flotation rapidly while maintaining its physical integrity in gastrointestinal fluids for prolonged periods.

Another embodiment discloses oral controlled release pharmaceutical composition for delivering Bepotastine to an environment of use, wherein the composition comprises (a) a wall comprising a composition that is permeable to the passage of fluid and is substantially impermeable to the passage of Bepotastine, which wall surrounds and forms; (b) a compartment comprising (i) a drug layer comprising Bepotastine, release controlling agents and optionally one osmagent; and (ii) a push layer in contact with the drug layer in the compartment, which push layer, in the presence of fluid that enters the controlled release pharmaceutical composition, increases in dimension and pushes the drug layer from the controlled release pharmaceutical composition; and (d) at least one exit means in the wall for delivering the drug from the said composition at a controlled rate over a period of time.

Orifice as herein comprises means and methods suitable for releasing the active ingredient or drug from the osmotic system. The orifice may be formed by mechanical drilling or laser drilling.

The oral controlled release pharmaceutical compositions of Bepotastine exhibit release of Bepotastine in vitro that is not less than 50% between 0.5 to 12.0 hours, preferably between 1.0 to 10.0 hours and most preferably between 2.0 to 8.0 hours.

A suitable dissolution test is carried out to test the release of Bepotastine uses USP Apparatus II (Paddle) at 50 rpm with 900 ml of 0.1 N Hydrochloric acid at 37° C. or uses USP Apparatus II (Paddle) at 50 rpm with 900 ml of phosphate buffer at pH 6.8 at 37° C.

The dissolution test may also be carried out using USP Apparatus I (Basket) at 100 rpm with 900 ml of 0.1 N Hydrochloric acid or with 900 ml of phosphate buffer at pH 6.8 at 37° C.

The oral controlled release pharmaceutical compositions of Bepotastine or pharmaceutically acceptable salts thereof and at least one release controlling agent, wherein, pharmaceutical composition administered once daily, is substantially bioequivalent to conventional immediate release composition of Bepotastine administered twice daily.

Another embodiment provides oral controlled release pharmaceutical compositions of Bepotastine or pharmaceutically acceptable salts thereof and at least one release controlling agent, wherein pharmaceutical compositions exhibit relative bioavailability based on the area under the plasma concentration curve (AUC) for the for the 24 hours after once a day administration in human subjects, of between about 50 to about 150 compared with commercially available Talion immediate release tablets containing Bepotastine administered twice daily.

Yet another provides oral controlled release pharmaceutical compositions of Bepotastine or pharmaceutically acceptable salts thereof and at least one release controlling agent, wherein pharmaceutical compositions exhibit a relative Cmax, after once a day administration in human subjects, of between about 50 to about 150 compared with commercially available Talion immediate release tablets containing Bepotastine administered twice daily.

The oral controlled release pharmaceutical compositions of Bepotastine or pharmaceutically acceptable salts thereof and at least one release controlling agent wherein pharmaceutical composition is bioequivalent to conventional immediate release composition of Bepotastine administered twice daily under fed conditions where bioequivalence is established by (a) a 90% confidence interval for AUC which is between 80% and 125%, and (b) a 90% confidence interval for $C_{max}$, which is between 80% and 125%.

Another embodiment, provides oral controlled release pharmaceutical composition of Bepotastine or pharmaceutically acceptable salts thereof and at least one release controlling agent wherein, the composition provides mean geometric $AUC_{(0-24)}$ of Bepotastine in the range of about 180 ng·h/ml to about 560 ng·h/ml at 24 hours after single dose administration of composition containing 12.5 mg Bepotastine.

Yet another embodiment provides oral controlled release pharmaceutical composition of Bepotastine or pharmaceutically acceptable salts thereof and at least one release controlling agent, wherein the composition provides peak plasma concentration ($C_{max}$) in the range of about 20 ng/ml to about 70 ng/ml at 24 hours after single dose administration of composition containing 12.5 mg Bepotastine.

Another embodiment, provides oral controlled release pharmaceutical composition of Bepotastine or pharmaceutically acceptable salts thereof and at least one release controlling agent wherein, the composition provides mean geometric $AUC_{(0-24)}$ of Bepotastine in the range of about 350 ng·h/ml to about 1100 ng·h/ml at 24 hours after single dose administration of composition containing 25 mg Bepotastine.

Another embodiment provides oral controlled release pharmaceutical composition of Bepotastine or pharmaceutically acceptable salts thereof and at least one release controlling agent wherein, the composition provides peak plasma concentration in the range of about 40 ng/ml to about 140 ng/ml at 24 hours after single dose administration of composition containing 25 mg Bepotastine.

The oral controlled release pharmaceutical compositions of Bepotastine which is substantially bioequivalent to the conventional immediate release composition of Bepotastine administered twice daily will provide the effective plasma concentration as achieved by the twice daily administration and thus minimise the variations in plasma concentration of Bepotastine.

"Bioavailability" as used herein, refers to the rate and extent of uptake of the active ingredient or active agent from a drug product.

"Bioequivalence" as used herein, refers to the equivalent release of the same drug substance from two or more drug products or formulations. This leads to an equivalent rate and extent of absorption from these formulations. For example, different compositions exhibiting bioequivalence to each other are bioequivalent.

Bioequivalence can be determined by an in vivo study comparing a pharmacokinetic parameter for the two compositions. Parameters that may be used in bioequivalence studies are Tmax, Cmax, $AUC_{0-inf}$, $AUC_{0-t}$. In the present context, substantial bioequivalence of two compositions is established by 90% confidence intervals (CI) of between 0.80 and 1.25 for $AUC_{(0-24)}$ and $C_{max}$ under fed condition.

In a specific embodiment, bioequivalence of the once a day controlled release pharmaceutical compositions of Bepotastine or pharmaceutically acceptable salts thereof and at least one release controlling agent with twice daily Talion® 5 mg immediate release tablets under fed condition is determined according to the US Federal Drug Administration's (FDA) guidelines and criteria.

As used herein, "about" refers to a range of values ±10% of a specified value.

Summary of Relative Bioavailability Studies

A comparison of the relative bioavailability of controlled release pharmaceutical composition of Bepotastine prepared according to example 12 and example 13 with Talion® 5 mg immediate release tablet was carried out in 8 healthy adult male volunteers under standard fed conditions.

Results of the studies under fed conditions are as indicated in the Table 1 and 2 below:

TABLE 1

Results of relative bioavailability studies of once a day (QD) controlled release pharmaceutical composition of Bepotastine prepared as Example 12 under fed conditions with twice daily (BID) Talion ® 5 mg immediate release tablet.

| Treatment | $AUC_{(0-24)}$ (ng · h/ml) | $C_{max}$ (ng/ml) | $T_{max}$ (hr) |
| --- | --- | --- | --- |
| Example 12 (Test) | 354.1 | 41.8 | 5.2 |
| Talion ® Tablet 5 mg immediate release BID (Reference) | 372.6 | 43.6 | 1.75, 13.0 |
| Relative BA (% T/R) | 95.0 | 95.8 | — |

Results of table 1 indicate that composition of example 12 when administered once a day is substantial bioequivalent to Talion® 5 mg immediate release tablet BID. The pharmacokinetic profile shows that initial rate of absorption of composition prepared in accordance to example 12 is comparable to that of first IR dose Talion® 5 mg immediate release tablet. T/R values for $C_{max}$ is 95.8% indicates lesser propensity towards peak exposure related side-effects with once a day controlled release pharmaceutical composition of Bepotastine when compared to release profile of Talion® 5 mg immediate release tablet when administered twice daily. The study also eliminates frequent dosing of Bepotastine.

TABLE 2

Results of relative bioavailability studies of once a day (QD) controlled release pharmaceutical composition of Bepotastine prepared as Example 13 under fed conditions with twice daily (BID) Talion ® 5 mg immediate release tablet.

| Treatment | $AUC_{(0-24)}$ (ng · h/ml) | $C_{max}$ (ng/ml) | $T_{max}$ (hr) |
|---|---|---|---|
| Example 13 (Test) | 376.0 | 37.8 | 7.0 |
| Talion ® Tablet 5 mg immediate release BID (Reference) | 372.6 | 43.6 | 1.75, 13.0 |
| Relative BA (% T/R) | 100.9 | 86.6 | — |

Results of table 2 indicate that composition of example 13 when administered once a day is substantial bioequivalent to Talion® 5 mg immediate release tablet BID. The pharmacokinetic profile shows that composition of example 13 eliminates peaks and trough as observed in Talion® 5 mg immediate release tablet when administered twice daily. T/R values for $C_{max}$ is 86.6% indicates lesser propensity towards peak exposure related side-effects with once a day controlled release pharmaceutical composition of Bepotastine when compared to release profile of Talion® 5 mg immediate release tablet when administered twice daily. The study also eliminates frequent dosing of Bepotastine.

The oral controlled release pharmaceutical compositions comprising Bepotastine can be used for the treatment of allergic rhinitis and treatment of pruritus caused by urticaria using a once-a-day dosing frequency.

It must be noted that as used in this specification and in the appended claims, the singular forms also include the plural unless the context clearly dictates otherwise.

The following non-limiting examples illustrate the various embodiments of the invention.

Example 1

| Sr. No. | Ingredient | Quantity (mg/Tab) |
|---|---|---|
| | Intragranular | |
| 1 | Bepotastine Besilate | 10.0 |
| 2 | Lactose Monohydrate | 139.0 |
| 3 | Methacrylic Acid Copolymer, Type C | 25.0 |
| 4 | Hydroxypropyl Methyl Cellulose E10MCR | 90.0 |
| 5 | Hydroxy Propyl Cellulose EXF | 3.0 |
| 6 | Purified Water | q.s |
| | Extragranular | |
| 7 | Colloidal silicon Dioxide 200 | 2.0 |
| 8 | Magnesium Stearate | 1.0 |
| Total Core Weight | | 270.0 |
| 9 | Opadry Pink | 8.0 |
| 10 | Purified Water | q.s |
| Total Weight of Coated Tablet | | 278.0 |

Brief Manufacturing Procedure:
1. The weighed quantity of Bepotastine Besilate along with Lactose Monohydrate, Hydroxypropyl Methyl Cellulose E10MCR, Methacrylic Acid Copolymer, Type C, Hydroxypropyl Cellulose EXF is sifted through 40# SS Sieve.
2. The blend of step 1 is loaded in rapid mixer granulator and dry mixed for 10 minutes at impeller fast speed.
3. The blend of step 2 is granulated using purified water.
4. The wet granules of step 3 are dried in tray dryer at 60° C. inlet till its LOD reaches 1.8% w/w.
5. The dried granules of step 4 are passed through 25# SS Sieve.
6. The extragranular quantity of Colloidal Silicon Dioxide 200 is passed through 40# SS Sieve.
7. The granules of step 5 are mixed with Colloidal Silicon Dioxide of step 6 for 5 minutes.
8. The blend of step 7 is lubricated with Magnesium Stearate (passed through 40# SS Sieve) for 3 minutes.
9. The lubricated blend of step 8 is compressed using 9.1 mm round shape punches with average fill weight of 270 mg and suitable physical parameters.
10. The compressed tablets of step 9 are coated using 10% w/w aqueous dispersion of OPADRY pink with 3.0% w/w weight gain.

Example 2

| Sr. No. | Ingredients | Quantity (mg/Tab) |
|---|---|---|
| | Intragranular | |
| 1 | Bepotastine Besilate | 10.0 |
| 2 | Lactose Monohydrate | 124.0 |
| 3 | Hydroxypropyl Methyl Cellulose K15 MCR | 40.0 |
| 4 | Hydroxypropyl Methyl Cellulose K4 MCR | 2.0 |
| 5 | Hydroxypropyl Cellulose EXF | 3.0 |
| 6 | Sodium Starch Glycolate | 3.0 |
| 7 | Purified Water | q.s |
| | Extragranular | |
| 8 | Colloidal Silicon Dioxide 200 | 2.0 |
| 9 | Magnesium Stearate | 1.0 |
| Core Total weight | | 203.0 |
| | Coating 5% w/w | |
| 10 | Ethyl Cellulose 10 Cps | 7.5 |
| 11 | Hydroxypropyl Methyl Cellulose E-5 | 5 |
| 12 | Triethyl Citrate | 3.74 |
| 13 | Isopropyl alcohol (IPA) | q.s |
| 14 | Dichloromethane (DCM) | q.s |
| Total weight | | 219.2 |

Brief Manufacturing Procedure:
1. The weighed quantity of Bepotastine Besilate along with Lactose Monohydrate, Hydroxypropyl Methyl Cellulose K4MCR, Hydroxypropyl Methyl Cellulose K15 M, Hydroxypropyl Cellulose EXF and Sodium Starch Glycolate is sifted through 40# SS Sieve.
2. The blend of step 1 is loaded in rapid mixer granulator and dry mixed for 5 minutes at impeller fast speed.
3. The blend of step 2 is granulated using purified water.
4. The wet granules of step 3 are dried in tray dryer at 60° C. inlet till its LOD reaches 1.5% w/w.
5. The dried granules of step 4 are passed through 25# SS Sieve.
6. The extragranular quantity of Colloidal Silicon Dioxide 200 is sifted through 40# SS Sieve.
7. The granules of step 5 are mixed with Colloidal Silicon Dioxide of step 6 for 5 minutes.

8. The blend of step 7 is lubricated with Magnesium Stearate (passed through 40# SS Sieve) for 3 minutes.
9. The lubricated blend of step 8 is compressed using 9.1 mm round shape punches with average fill weight of 250 mg and suitable physical parameters.

Coating:

10. The required quantity of Ethyl Cellulose 10 cps and Hydroxypropyl Methyl Cellulose E-5 is dissolved in IPA & DCM (50:50) mixture with continuous stirring till the clear solution is formed.
11. Triethyl Citrate is added in Step 10 with continuous stirring for 20 minutes.
12. The tablets of step 9 are coated using coating solution of step 11 till 8% w/w weight gain is obtained using suitable coating parameters.
13. The tablets are cured in coating pan at 50° C. inlet temperature for 15-20 minutes.

Example 3

| Sr. No. | Ingredients | Quantity (mg/Tab) |
|---|---|---|
| | Intragranular | |
| 1 | Bepotastine Besilate | 10.0 |
| 2 | Mannitol | 84.0 |
| 3 | Ethyl Cellulose 10 cps | 70.0 |
| 4 | Methacrylic Acid Copolymer, Type C | 30.0 |
| 5 | Hydroxypropyl Cellulose EXF | 3.0 |
| | Extragranular | |
| 6 | Colloidal Silicon Dioxide 200 | 2.0 |
| 7 | Magnesium Stearate | 1.0 |
| Total Core Weight | | 200.0 |
| 8 | Opadry Pink | 6.0 |
| 9 | Purified Water | q.s |
| Total Weight of Coated Tablet | | 206.0 |

Brief Manufacturing Procedure:

1. The weighed quantity of Bepotastine Besilate along with Mannitol, Ethyl Cellulose 10 cps FP, Methacrylic Acid Copolymer, Type C, Hydroxypropyl Cellulose EXF is sifted through 40# SS Sieve.
2. The blend of step 1 is loaded in rapid mixer granulator and dry mixed for 5 minutes at impeller fast speed.
3. The blend of step 2 is granulated using purified water.
4. The wet granules of step 3 are dried in tray dryer at 60° C. inlet till its LOD reaches 1.5% w/w.
5. The dried granules of step 4 are passed through 25# SS Sieve.
6. The extragranular quantity of Colloidal Silicon Dioxide 200 is passed through 40# SS Sieve.
7. The granules of step 5 are mixed with Colloidal Silicon Dioxide of step 6 for 5 minutes.
8. The blend of step 7 is lubricated with Magnesium Stearate (passed through 40# SS Sieve) for 3 minutes.
9. The lubricated blend of step 8 is compressed using 8.2 mm round shape punches with average fill weight of 200 mg and suitable physical parameters.
10. The compressed tablets of step 9 are coated using 10% w/w aqueous dispersion of OPADRY pink with 3.0% w/w weight gain.

Example 4

| Sr. No. | Ingredients | Quantity % w/w |
|---|---|---|
| | Controlled Release Layer | |
| 1 | Bepotastine | 6.0 |
| 2 | Polyvinyl pyrrolidone | 2.5 |
| 3 | Poloxamer | 2.5 |
| 4 | Hydroxy propyl methyl cellulose | 50.0 |
| 5 | Lactose monohydrate | 5.5 |
| 6 | Polyethylene oxide | 5.0 |
| 7 | Microcrystalline cellulose | 5.0 |
| 8 | Magnesium stearate | 0.5 |
| 9 | Alcohol/dichloromethane mixture | q.s |
| | Bioadhesive Layer | |
| 10 | Hydrogenated vegetable oil | 5.0 |
| 11 | Polyethylene oxide | 8.0 |
| 12 | Hydroxy propyl methyl cellulose | 9.0 |
| 13 | Silicon dioxide | 0.5 |
| 14 | Magnesium stearate | 0.5 |
| 15 | Opadry coat | 2-5% of core weight |

Brief Manufacturing Procedure:

Controlled Release Layer

1. Hydroxy propyl methyl cellulose, polyethylene oxide, lactose monohydrate and microcrystalline cellulose are sifted through suitable sieve and mixed in a rapid mixer granulator.
2. Bepotastine, poloxamer and polyvinyl pyrrolidone are dissolved in alcohol/dichloromethane mixture.
3. Mixture of step 1 is granulated with solution of step 2.
4. The wet granules are dried and sifted through a suitable sieve.
5. The granules are lubricated using magnesium stearate.

Mucoadhesive Layer

6. Lactose monohydrate, hydrogenated vegetable oil, polyethylene oxide, hydroxy propyl methyl cellulose and silicon dioxide are sifted and mixed.
7. The blend of step 6 is lubricated using magnesium stearate.
8. The blend of step 5 and step 7 is compressed into bilayer tablets using suitable shaped punches and dies.
9. The tablets are coated using Opadry coat.

Example 5

| Sr. No. | Ingredients | Quantity % w/w |
|---|---|---|
| 1 | Bepotastine | 5.0 |
| 2 | Hydroxy propyl cellulose | 4.0 |
| 3 | Poloxamer | 5.0 |
| 4 | Hydroxy propyl methyl cellulose | 30.0 |
| 5 | Hydrogenated vegetable oil | 15.0 |
| 6 | Lactose monohydrate | 24.0 |
| 7 | Microcrystalline cellulose | 15.0 |
| 8 | Colloidal silicon dioxide | 1.0 |
| 9 | Magnesium stearate | 1.0 |
| | Coating | |
| 10 | Alcohol/dichloromethane mixture | q.s |
| 11 | Ammonio methacrylate copolymer- Type A | 5.0 |
| 12 | Ammonio methacrylate copolymer- Type B | 5.0 |
| 13 | Triethyl citrate | 1.0 |
| 14 | Isopropyl alcohol/acetone mixture | q.s |

Brief Manufacturing Procedure:
1. Microcrystalline cellulose and lactose monohydrate is sifted through 40 # SS sieve.
2. Bepotastine, poloxamer and hydroxy propyl cellulose is dissolved in alcohol/dichloromethane mixture.
3. The dry mix of step 1 is granulated using solution of step 2 in rapid mixer granulator.
4. The wet granules are dried and the dried granules are sifted through 25 # SS sieve.
5. The dried granules of step 4 are mixed with hydroxy propyl methyl cellulose and hydrogenated vegetable oil and colloidal silicon dioxide.
6. The granules of step 5 are lubricated using magnesium stearate.
7. The lubricated blend is compressed using suitable tooling.
8. The compressed tablets are coated using solution of ammonio methacrylate copolymer-type A, ammonio methacrylate copolymer-type B and triethyl citrate in isopropyl alcohol/acetone mixture.

Example 6

| Sr. No. | Ingredients | Quantity % w/w |
|---|---|---|
| 1 | Bepotastine | 5.0 |
| 2 | Polyvinyl pyrrolidone | 5.0 |
| 3 | Sodium lauryl sulfate | 5.0 |
| 4 | Mannitol | 45.0 |
| 5 | Lactose monohydrate | 10.0 |
| 6 | Microcrystalline cellulose | 10.0 |
| 7 | Magnesium stearate | 1.0 |
| 8 | Purified water | qs |
| 9 | Cellulose acetate | 15.0 |
| 10 | Polyethylene glycol | 3.0 |
| 11 | Triacetin | 1.0 |
| 12 | Acetone | q.s |

Brief Manufacturing Procedure:
1. All the ingredients are sifted separately with suitable sieve.
2. Bepotastine, Mannitol and lactose monohydrate are mixed and granulated using aqueous solution of polyvinyl pyrrolidone.
3. The wet granules of step 2 are dried and the dried granules are sifted through 25 # SS sieve.
4. The dried sifted granules are blended with microcrystalline cellulose, sodium lauryl sulfate.
5. The blend of step 4 is lubricated with magnesium stearate.
6. The lubricated blend is compressed.
7. Cellulose acetate is dissolved in acetone along with triacetin and polyethylene glycol under stirring.
8. The compressed tablets of step 6 are coated using coating solution of step 7.
9. The tablets are drilled with tablet laser driller machine to form suitable size orifice.

Example 7

| Sr No | Ingredients | Quantity % w/w |
|---|---|---|
| 1 | Bepotastine | 5.0 |
| 2 | Low substituted hydroxy propyl cellulose | 10.0 |
| 3 | Hydroxy propyl methyl cellulose | 40.0 |
| 4 | Polyvinyl acetate | 15.0 |

-continued

| Sr No | Ingredients | Quantity % w/w |
|---|---|---|
| 5 | Lactose monohydrate | 15.0 |
| 6 | Microcrystalline cellulose | 14.0 |
| 7 | Magnesium stearate | 1.0 |
| 8 | Purified water | q.s |
| 9 | Opadry coat | 2-5% of core weight |

Brief Manufacturing Procedure:
1. Bepotastine, microcrystalline cellulose and lactose monohydrate are sifted through 40 # SS sieve and mixed.
2. The above blend is granulated using aqueous solution of low substituted hydroxy propyl cellulose.
3. The wet granules are dried and the dried granules are sifted through 20 # SS sieve.
4. The dried granules of step 3 are mixed with hydroxy propyl methyl cellulose and polyvinyl acetate.
5. The granules of step 4 are lubricated using magnesium stearate.
6. The lubricated blend is compressed using suitable sized & shaped punch.
7. The compressed tablets are coated using Opadry coating dispersion.

Example 8

| Sr No | Ingredients | Quantity (mg/Tab) |
|---|---|---|
| 1 | Bepotastine | 5.0 |
| 2 | Low substituted hydroxy propyl cellulose | 10.0 |
| 3 | Hydroxy propyl methyl cellulose | 40.0 |
| 4 | Polyvinyl acetate | 15.0 |
| 5 | Fumaric acid | 2.0 |
| 6 | Lactose monohydrate | 15.0 |
| 7 | Microcrystalline cellulose | 14.0 |
| 8 | Magnesium stearate | 1.0 |
| 9 | Purified water | q.s |
| 10 | Opadry coat (non-functional) | 2-5% of core weight |

Brief Manufacturing Procedure:
1. Bepotastine, microcrystalline cellulose and lactose monohydrate are sifted through 40 # SS sieve and mixed.
2. The above blend is granulated using aqueous solution of low substituted hydroxy propyl cellulose as binder.
3. The wet granules dried and the dried granules are sifted through 20 # SS sieve.
4. The dried granules of step 3 are mixed with hydroxy propyl methyl cellulose, polyvinyl acetate and fumaric acid.
5. The granules of step 4 are lubricated using magnesium stearate.
6. The lubricated blend is compressed using suitable size & shape punch.
7. The compressed tablets are coated using Opadry coating dispersion.

Example 9

| Sr. No. | Ingredients | Quantity (mg/Tab) |
|---|---|---|
| | Intragranular | |
| 1 | Bepotastine Besilate | 20.0 |
| 2 | Lactose monohydrate | 99.0 |
| 3 | Methacrylic Acid Copolymer, Type C | 25.0 |
| 4 | Hydroxypropyl Methyl Cellulose E10MCR | 120.0 |
| 5 | Hydroxy Propyl Cellulose EXF | 3.0 |
| | Extragranular | |
| 6 | Colloidal silicon Dioxide 200 | 2.0 |
| 7 | Magnesium Stearate | 1.0 |
| Total Core Weight | | 270.0 |
| 8 | Opadry Pink | 8.0 |
| 9 | Purified Water | q.s |

Brief Manufacturing Procedure:
1. The weighed quantity of Bepotastine Besilate along with Lactose Monohydrate, Hydroxypropyl Methyl Cellulose E10MCR, Methacrylic Acid Copolymer Type C, Hydroxypropyl Cellulose EXF is sifted through 40# SS Sieve.
2. The blend of step 1 is loaded in Conta blender and dry mixed for 20 minutes.
3. The weighed quantity of Colloidal Silicon Dioxide 200 is passed through 40# SS Sieve and added to blend of step 2 and dry mixed it 10 minutes.
4. The blend of step 3 is lubricated with Magnesium Stearate (passed through 40# SS Sieve) for 3 minutes in Conta blender.
5. The lubricated blend of step 4 is compressed using 9.1 mm round shape punches with average fill weight of 270 mg and suitable physical parameters.
6. The compressed tablets of step 5 are coated using 10% w/w aqueous dispersion of OPADRY pink with 3.0% w/w weight gain.

Example 10

| Sr. No. | Ingredients | Quantity % w/w |
|---|---|---|
| | Drug Layer | |
| 1 | Bepotastine Besilate | 2-20 |
| 2 | Hydroxy Ethylcellulose | 1-10 |
| 3 | Mannitol | 5-25 |
| 4 | Polyethylene oxide | 10-60 |
| 5 | Sodium lauryl sulfate | 0-10 |
| 6 | Magnesium stearate | 1-2 |
| 7 | Isopropyl alcohol | q.s. |
| | Push Layer | |
| 8 | Polyethylene oxide | 10-50 |
| 9 | Mannitol | 10-40 |
| 10 | Hydroxypropyl methyl cellulose | 10-20 |
| 11 | Hydroxypropyl cellulose | 2-5 |
| 12 | Magnesium stearate | 1-2 |
| | Coating (For 2-10% wt. gain) | |
| 13 | Cellulose acetate | 10-30 |
| 14 | Dibutyl sebacate | 2-10 |
| 15 | Acetone | q.s. |

Brief Manufacturing Procedure:
Active Layer:
1. Bepotastine Besilate, mannitol and Polyethylene oxide are sifted separately and mixed.
2. Mixture of step is granulated with Hydroxy Ethylcellulose solution in IPA.
3. The wet granules of step 2 are dried and sifted through suitable sieve.
4. The granules of step 3 are lubricated using magnesium stearate.

Push Pull Layer
5. Polyethylene oxide, mannitol, Hydroxypropyl methyl cellulose and Hydroxypropyl cellulose are sifted and mixed.
6. The blend of step 5 is lubricated with magnesium stearate.

Compression
7. Granules of Step 4 and Step 6 are compressed as bilayered tablet using suitable size and shape punch.

Coating
8. Cellulose acetate is dissolved in acetone with stirring along with dibutyl sebacate.
9. The compressed tablets of Step 7 are coated using coating solution of step 8.

Pore Forming
10. An orifice is drilled on the coated tablets with laser drilling technology.

Example 11

| Sr. No. | Ingredients | Quantity (mg/Tablet) |
|---|---|---|
| | Controlled Release Matrix Layer | |
| 1 | Bepotastine Besilate | 8.0 |
| 2 | Hydroxypropyl Methylcellulose E5 | 20.00 |
| 3 | Hydroxypropyl Methylcellulose K100 LVCR | 100 |
| 4 | Hydroxypropyl Methylcellulose K100 MCR | 20 |
| 5 | Polyoxyethylene oxide (PEOWSR 303) | 10 |
| 6 | Lactose Monohydrate | 95 |
| 7 | Microcrystalline cellulose | 120.5 |
| 8 | Magnesium stearate | 2.0 |
| 9 | Colloidal silicon dioxide | 2.0 |
| 10 | Purified water: Isopropyl alcohol mixture | |
| | Inert Layer | |
| 11 | Polyoxyethylene oxide | 20 |
| 12 | Hydrogenated vegetable oil | 27 |
| 13 | Lactose monohydrate | 15 |
| 14 | Hydroxypropyl Methylcellulose E5 | 50 |
| 15 | Hydroxypropyl Methylcellulose K100 LVCR | 35 |
| 16 | Colloidal Silicon dioxide | 1.5 |
| 17 | Magnesium Stearate | 1.5 |
| | Controlled Release Coating | |
| 18 | Ethyl cellulose 7 cps | 6.0 |
| 19 | Hydroxypropyl Methylcellulose | 6.0 |
| 20 | Triethyl citrate | 1.2 |
| 21 | Isopropyl alcohol: DCM mixture | qs |
| | Drug Layer | |
| 22 | Bepotastine Besilate | 2.0 |
| 23 | Opadry | 18 |
| 24 | Water | qs |

Brief Manufacturing Procedure:
Controlled Release Matrix Layer
1. Bepotastine Besilate, lactose monohydrate and Hydroxypropyl Methylcellulose K100LVCR are sifted through suitable sieve.
2. The above mixture is granulated using Hydroxypropyl Methylcellulose E5 solution.

3. The wet granules of step 2 are dried and sifted through suitable sieve.
4. Sifted Hydroxypropyl Methylcellulose K4MCR, Polyoxyethylene oxide, microcrystalline cellulose and Colloidal Silicon Dioxide are added to granules of step 3 and mixed well.
5. The granules of step 4 are lubricated with 60# passed magnesium stearate.

Inert Layer

6. Hydroxypropyl Methylcellulose, Hydrogenated vegetable oil and lactose monohydrate are sifted and mixed.
7. The above blend is granulated with water and Isopropyl alcohol mixture.
8. The wet granules of step 7 are dried and sifted through suitable sieve.
9. Polyoxyethylene oxide, Hydroxypropyl Methylcellulose and Colloidal Silicon Dioxide are sifted and mixed with the granules of step 8.
10. The blend of step 9 is lubricated with 60# passed magnesium stearate.
11. Granules of step 5 and step 10 are compressed into bilayer tablets using suitable punches and dies.

Controlled Release Coating

12. Ethyl cellulose, Hydroxypropyl Methylcellulose and Triethyl citrate are dissolved in Isopropyl alcohol and DCM mixture.
13. The compressed tablets of Step 11 are coated using coating solution of step 12.

Drug Layer

14. Bepotastine Besilate is dispersed in dispersion of Opadry in water.
15. The coated tablets of Step 13 are coated using coating solution of step 14.

Example 12

| S. No | Ingredient | Quantity (Mg/Tab) |
|---|---|---|
| | Drug Layer | |
| | Intragranular | |
| 1 | Bepotastine Besilate | 10.0 |
| 2 | Lactose Monohydrate | 154.0 |
| 3 | Hydroxypropyl Methylcellulose K-15M CR | 30.0 |
| 4 | Sodium starch glycolate | 3.0 |
| 5 | Hydroxypropylcellulose EXF | 3.0 |
| 6 | Purified Water | q.s. |
| | Extra granular | |
| 7 | Colloidal Silicon dioxide | 2.0 |
| 8 | Magnesium Stearate | 1.0 |
| Total Weight (A) | | 203.0 |
| | Bioadhesive Layer | |
| 9 | Hydroxypropyl Methylcellulose K-15M CR | 115.4 |
| 10 | Polyethylene oxide | 115.4 |
| 11 | Lactose Monohydrate | 60.0 |
| 12 | Colloidal silicone dioxide | 5.8 |
| 13 | Magnesium Stearate | 3.5 |
| Total Weight (B) | | 300.0 |
| Total Weight (A + B) | | 503.0 |
| | CR Coating (5% w/w) | |
| 14 | Ethyl Cellulose 10 cps | 11.5 |
| 15 | Hydroxypropyl Methylcellulose 3 cps | 7.7 |
| 16 | Triethyl citrate | 5.8 |

| S. No | Ingredient | Quantity (Mg/Tab) |
|---|---|---|
| 17 | Isopropyl alcohol | q.s. |
| 18 | Dichloromethane | q.s. |
| Total Weight | | 528.0 |
| | IR Active coat (2.5 mg of Bepotastine) | |
| 19 | Bepotastine Besilate | 2.5 |
| 20 | Hydroxypropyl Methylcellulose 5 cps | 6.0 |
| 21 | Triethyl citrate | 1.5 |
| 22 | Ethanol | q.s. |
| 23 | Water | q.s. |
| Total Weight | | 538.0 |

Brief Manufacturing Procedure:

Drug Layer

1. Weighed quantity of Bepotastine Besilate along with Lactose, Hydroxypropyl Methylcellulose, Sodium starch glycolate, Hydroxypropylcellulose are sifted through 40# SS Sieve.
2. The blend of step 1 is loaded in Rapid Mixture Granulator and mixed for 10 minutes.
3. The blend of step 2 is granulated using purified water.
4. The wet granules of step 3 are dried in tray dryer at 60° C. inlet till its LOD reaches 1.5% w/w.
5. The dried granules of step 4 are passed through 20# SS Sieve.
6. The extra granular quantity of Colloidal silicon dioxide is passed through 40# SS Sieve.
7. The granules of step 5 are mixed with Colloidal silicon dioxide of step 6 for 5 minutes.
8. The blend of step 7 is lubricated with Magnesium stearate (passed through 40# SS Sieve).

Bioadhesive Layer:

9. Weighed quantity of Hydroxypropyl Methylcellulose, Polyethylene oxide, Lactose and Colloidal silicon dioxide are sifted together through 40# SS sieve.
10. The blend of step 9 is lubricated with Magnesium stearate (passed through 40# SS Sieve) for 3 minutes.
11. The lubricated blend of step 8 and step 10 is compressed into bilayer tablets.

CR Coating (2.5%)

12. Weighed quantity of Ethyl cellulose, Hydroxypropyl Methylcellulose and Triethyl citrate are dissolved in sufficient quantity of Isopropyl alcohol and Dichloromethane mixture with continuous stirring.
13. Tablets of step 11 are coated using coating solution of step 12 to get 5.0% w/w weight buildup.

Active IR Coating

14. Weighed quantity of Bepotastine Besilate, Hydroxypropyl Methylcellulose and Triethyl citrate are dissolved in sufficient quantity of mixture of Water and Ethanol with continuous stirring.
15. The tablets of step 13 are coated using coating solution of step 14 for active drug over coating of 2.5 mg per tablet.

Example 13

| S. No | Ingredient | Quantity (Mg/Tab) |
|---|---|---|
| | Drug Layer | |
| | Intra granular | |
| 1 | Bepotastine Besilate | 12.5 |
| 2 | Partially Pregelatinised Starch | 30.0 |
| 3 | Copolymer methacrylic acid and ethyl acrylate (Eudragit L100-55) | 40.0 |
| 4 | Hydroxypropyl Methylcellulose K-15M CR | 10.0 |
| 5 | Hydroxypropyl Methylcellulose E 10M CR | 100.0 |
| 6 | Lactose Monohydrate | 100.0 |
| 7 | Hydroxypropylcellulose EXF | 5.0 |
| 8 | Purified Water | q.s. |
| | Extra granular | |
| 9 | Partially Pregelatinised Starch | 15.0 |
| 10 | Carbomer | 10.0 |
| 11 | Lactose monohydrate | 17.5 |
| 12 | Colloidal silicone dioxide | 3.0 |
| 13 | Magnesium Stearate | 2.0 |
| Total Weight (A) | | 345.0 |
| | Bioadhesive Layer | |
| 14 | Hydroxypropyl Methylcellulose K-15M CR | 96.2 |
| 15 | Polyethylene oxide | 96.2 |
| 16 | Lactose Monohydrate | 50.0 |
| 17 | Colloidal silicone dioxide | 4.8 |
| 18 | Magnesium Stearate | 2.9 |
| Total Weight (B) | | 250.0 |
| Total Weight (A + B) | | 595.0 |

Brief Manufacturing Procedure:

Drug Layer

1. Weighed quantity of Bepotastine Besilate along with Lactose Monohydrate, Partially Pregelatinized Starch, Eudragit, Hydroxypropyl Methylcellulose E10MCR, Hydroxypropyl Methylcellulose K15 M, Hydroxypropylcellulose EXF are sifted through 40# SS Sieve.
2. The blend of step 1 is loaded in Rapid Mixture Granulator and mixed for 10 minutes.
3. The blend of step 2 is granulated using purified water.
4. The wet granules of step 3 are dried in tray dryer at 60° C. inlet till its LOD reaches 1.5% w/w.
5. The dried granules of step 4 are passed through 20# SS Sieve.
6. The extra granular quantity of Partially pregelatinized starch, Carbopol 974P, Lactose monohydrate, Colloidal silicon dioxide is sifted through 40# SS Sieve.
7. The granules of step 5 are mixed with blend of step 6 for 5 minutes.
8. The blend of step 7 is lubricated with Magnesium stearate (passed through 40# SS Sieve) for 3 minutes.

Bioadhesive Layer:

9. Weighed quantity of Hydroxypropyl Methylcellulose K100 MCR, Polyethylene oxide, Lactose monohydrate and Colloidal silicone dioxide are sifted together through 40# SS sieve.
10. The blend of step 9 is lubricated with Magnesium stearate (passed through 40# SS Sieve) for 3 minutes.
11. The lubricated blend of step 8 and step 10 are compressed as bilayer tablets.

Example 14

| S. No | Ingredient | Quantity (Mg/Tab) |
|---|---|---|
| | Intra granular | |
| 1 | Bepotastine Besilate | 25.0 |
| 2 | Partially Pregelatinised Starch | 30.0 |
| 3 | Copolymer methacrylic acid and ethyl acrylate (Eudragit L100-55) | 40.0 |
| 4 | Hydroxypropyl Methylcellulose K-15M CR | 10.0 |
| 5 | Hydroxypropyl Methylcellulose E 10M CR | 100.0 |
| 6 | Lactose Monohydrate | 87.5 |
| 7 | Hydroxypropylcellulose EXF | 5.0 |
| 8 | Purified Water | q.s. |
| | Extra granular | |
| 9 | Partially Pregelatinised Starch | 15.0 |
| 10 | Carbomer | 10.0 |
| 11 | Lactose monohydrate | 17.5 |
| 12 | Colloidal silicone dioxide | 3.0 |
| 13 | Magnesium Stearate | 2.0 |
| Total Weight (A) | | 345.0 |
| | Bioadhesive Layer | |
| 14 | Hydroxypropyl Methylcellulose K-15M CR | 96.2 |
| 15 | Polyethylene oxide | 96.2 |
| 16 | Lactose Monohydrate | 50.0 |
| 17 | Colloidal silicone dioxide | 4.8 |
| 18 | Magnesium Stearate | 2.9 |
| Total Weight (B) | | 250.0 |
| Total Weight (A + B) | | 595.0 |

Brief Manufacturing Procedure:

Drug Layer

1. Weighed quantity of Bepotastine Besilate along with Lactose Monohydrate, Partially Pregelatinized Starch, Eudragit, Hydroxypropyl Methylcellulose E10MCR, Hydroxypropyl Methylcellulose K15 M, Hydroxypropylcellulose EXF are sifted through 40# SS Sieve.
2. The blend of step 1 is loaded in Rapid Mixture Granulator and mixed for 10 minutes.
3. The blend of step 2 is granulated using purified water.
4. The wet granules of step 3 are dried in tray dryer at 60° C. inlet till its LOD reaches 1.5% w/w.
5. The dried granules of step 4 are passed through 20# SS Sieve.
6. The extra granular quantity of Partially pregelatinized starch, Carbopol 974P, Lactose monohydrate, Colloidal silicon dioxide is sifted through 40# SS Sieve.
7. The granules of step 5 are mixed with blend of step 6 for 5 minutes.
8. The blend of step 7 is lubricated with Magnesium stearate (passed through 40# SS Sieve) for 3 minutes.

Bioadhesive Layer:

9. Weighed quantity of Hydroxypropyl Methylcellulose K100 MCR, Polyethylene oxide, Lactose monohydrate and Colloidal silicone dioxide are sifted together through 40# SS sieve.
10. The blend of step 9 is lubricated with Magnesium stearate (passed through 40# SS Sieve) for 3 minutes.
11. The lubricated blend of step 8 and step 10 are compressed as bilayer tablets.

The invention claimed is:

1. An oral controlled release pharmaceutical composition comprising Bepotastine or pharmaceutically acceptable salts thereof and at least one release controlling agent.

2. The oral controlled release pharmaceutical composition of claim 1, wherein the release controlling agent is selected from hydrophilic release controlling agents, hydrophobic release controlling agents or mixtures thereof.

3. The oral controlled release pharmaceutical composition of claim 2, wherein the hydrophilic release controlling agents are selected from hydroxypropyl methyl cellulose, hydroxypropyl cellulose, hydroxyethyl cellulose, polyethylene oxide, polyvinyl alcohol, polyvinylpyrrolidone, xanthan gum, guar gum, chitosan and its derivatives, carbomer, carrageenan, carboxymethyl cellulose, sodium alginate, polyglycolized glycerides, polyethylenglycol, or mixtures thereof.

4. The oral controlled release pharmaceutical composition of claim 2, wherein the hydrophobic release controlling agents are selected from polyvinyl acetate dispersion, cellulose esters, cellulose ethers and cellulose ester ethers ethyl cellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), and poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), waxes selected from beeswax, carnauba wax, paraffin wax, microcrystalline wax, and ozokerite; fatty alcohols selected from cetostearyl alcohol, stearyl alcohol, cetyl alcohol and myristyl alcohol; and fatty acid esters selected from glyceryl monostearate; glycerol monooleate, acetylated monoglycerides, tristearin, tripalmitin, cetyl esters wax, glyceryl palmitostearate, glyceryl behenate, and hydrogenated vegetable oils or mixture thereof.

5. The oral controlled release pharmaceutical composition of claim 1, wherein the Bepotastine or pharmaceutically acceptable salts thereof is present in an amount from about 5 mg to about 40 mg.

6. The oral controlled release pharmaceutical composition of claim 5, wherein the Bepotastine or pharmaceutically acceptable salts thereof is present in an amount from about 5 mg to about 25 mg.

7. An oral controlled release pharmaceutical composition comprising Bepotastine or pharmaceutically acceptable salts thereof and at least one release controlling agent, wherein the composition exhibits in vitro release of Bepotastine not less than about 50% in 12 hours, when dissolution is carried out in 900 ml of 6.8 pH Phosphate Buffer, USP apparatus Type I (basket) at 100 rpm or USP apparatus Type II (paddle) at 50 rpm.

8. An oral controlled release pharmaceutical composition comprising Bepotastine or pharmaceutically acceptable salts thereof and at least one release controlling agent, wherein the composition exhibits in vitro release of Bepotastine not less than about 70% in 12 hours, when dissolution is carried out in 900 ml of 0.1 N Hydrochloric acid, USP apparatus Type I (basket) at 100 rpm or USP apparatus Type II (paddle) at 50 rpm.

9. An oral controlled release pharmaceutical composition comprising Bepotastine or pharmaceutically acceptable salts thereof and at least one release controlling agent, wherein pharmaceutical composition administered once daily, is substantially bioequivalent to conventional immediate release composition of Bepotastine administered twice daily.

10. The oral controlled release pharmaceutical composition of claim 9, wherein pharmaceutical composition exhibits relative bioavailability based on the area under the plasma concentration curve (AUC) for the 24 hours after once a day administration in human subjects, of between about 50 to about 150 compared with commercially available Talion immediate release tablets containing Bepotastine administered twice daily.

11. The oral controlled release pharmaceutical composition of claim 9, wherein pharmaceutical composition exhibits a relative Cmax, after once a day administration in human subjects, of between about 50 to about 150 compared with commercially available Talion immediate release tablets containing Bepotastine administered twice daily.

12. The oral controlled release pharmaceutical composition of claim 9, wherein the composition provides a mean geometric $AUC_{(0-24)}$ of Bepotastine in the range of about 180 ng·h/ml to about 560 ng·h/ml at 24 hours after single dose administration of composition containing 12.5 mg Bepotastine or pharmaceutically acceptable salts thereof.

13. The oral controlled release pharmaceutical composition of claim 9, wherein the composition provides peak plasma concentration ($C_{max}$) in the range of about 20 ng/ml to about 70 ng/ml at 24 hours after single dose administration of composition containing 12.5 mg Bepotastine or pharmaceutically acceptable salts thereof.

14. The oral controlled release pharmaceutical composition of claim 9, wherein the composition provides mean geometric $AUC_{(0-24)}$ of Bepotastine in the range of about 350 ng·h/ml to about 1100 ng·h/ml at 24 hours after single dose administration of composition containing 25 mg Bepotastine or pharmaceutically acceptable salts thereof.

15. The oral controlled release pharmaceutical composition of claim 9, wherein, the composition provides wherein the composition provides peak plasma concentration ($C_{max}$) in the range of about 40 ng/ml to about 140 ng/ml at 24 hours after single dose administration of composition containing 25 mg Bepotastine or pharmaceutically acceptable salts thereof.

16. An oral controlled release pharmaceutical composition comprising Bepotastine or pharmaceutically acceptable salts thereof and at least one release controlling agent, wherein pharmaceutical composition is bioequivalent to conventional immediate release composition of Bepotastine administered twice daily under fed conditions where bioequivalence is established by (a) a 90% confidence interval for AUC which is between 80% and 125%, and (b) a 90% confidence interval for $C_{max}$, which is between 80% and 125%.

* * * * *